United States Patent
Boebel et al.

(10) Patent No.: US 6,824,544 B2
(45) Date of Patent: Nov. 30, 2004

(54) RESECTOSCOPE

(75) Inventors: Manfred Boebel, Bauschlolt (DE); Ludwig Bonnet, Knittlingen (DE); Sybille Brustle, Sternenfels (DE)

(73) Assignee: Richard Wolf GmbH, Knittlingen (DE)

( * ) Notice: Subject to any disclaimer, the term of this patent is extended or adjusted under 35 U.S.C. 154(b) by 0 days.

(21) Appl. No.: 10/396,173

(22) Filed: Mar. 25, 2003

(65) Prior Publication Data

US 2003/0181906 A1 Sep. 25, 2003

(30) Foreign Application Priority Data

Mar. 25, 2002 (DE) .......................................... 102 13 200

(51) Int. Cl.⁷ ............................................. A61B 18/18
(52) U.S. Cl. ..................... 606/46; 600/105; 600/130; 600/156
(58) Field of Search ..................... 600/105, 128–130, 600/156, 159; 606/41, 45–47

(56) References Cited

U.S. PATENT DOCUMENTS

| 3,835,842 | A | * | 9/1974 | Iglesias | ...................... 600/105 |
|---|---|---|---|---|---|
| 3,850,175 | A | | 11/1974 | Iglesias | .................. 128/303.15 |
| 3,900,022 | A | | 8/1975 | Widran | |
| 4,134,406 | A | * | 1/1979 | Iglesias | ........................ 606/46 |
| 4,343,300 | A | * | 8/1982 | Hattori | ........................ 600/109 |
| 4,998,527 | A | * | 3/1991 | Meyer | ......................... 600/104 |
| 5,527,331 | A | * | 6/1996 | Kresch et al. | ............... 606/170 |
| 5,836,909 | A | * | 11/1998 | Cosmescu | ..................... 604/35 |
| 2002/0072651 | A1 | * | 6/2002 | Vilos | ........................... 600/105 |
| 2003/0125607 | A1 | * | 7/2003 | Boebel et al. | .............. 600/136 |

FOREIGN PATENT DOCUMENTS

| DE | 3816049 | | 11/1988 | |
| EP | 0469266 B1 | | 2/1992 | |
| WO | WO 97/24074 | | 7/1997 | ........... A61B/17/39 |
| WO | WO 98/43531 | * | 10/1998 | |

* cited by examiner

Primary Examiner—Michael Peffley
(74) Attorney, Agent, or Firm—Cohen, Pontani, Lieberman & Pavane

(57) ABSTRACT

In the inside of an outer shank there are formed a supply channel and a discharge channel which extend parallel to the outer shank. The suction channel has a larger cross section than the supply channel.

14 Claims, 3 Drawing Sheets

RESECTOSCOPE

BACKGROUND OF THE INVENTION

1. Priority Claim

Priority is claimed for this invention and application, a corresponding application having been filed in Germany on Mar. 25, 2002, No. 102 13 200.3.

2. Field of the Invention

The invention relates to a resectoscope.

3. Description of the Related Art

With known resectoscopes, after a certain number of individual cuts with which tissue parts have been detached, it is usual to lead away the detached parts together through the outer shank of the resectoscope. For this it is first necessary to remove the so-called working insert from the outer shank of the resectoscope in order to be able to make available a sufficiently large cross section for leading away or suctioning away the tissue parts. This manner of proceeding is relatively time-consuming and is thus a burden to the patient.

From WO 98/43531 there is known a resectoscope whose cross section is divided into two parts by a separating wall, a larger part, which forms the suction channel, and a smaller part in which the optics shank is arranged and which serves as a supply channel. In the inside of the suction channel there is arranged the guide and actuation rod for a cutter loop. This leads to a narrowing of the suction channel; furthermore there exists the danger that tissue parts to be suctioned catch on the actuation elements for the cutter loop.

SUMMARY OF THE INVENTION

It is the object of the invention to create a resectoscope which permits an improved and quicker leading away of the detached tissue parts.

The resectoscope according to the invention comprises an outer shank in whose inside there is formed a supply channel and suction channel which extend parallel to the outer shank. A rinsing fluid is led through the supply channel into the body cavity to be operated on in order to produce an excess pressure in this. The rinsing fluid may be continuously supplied through the supply channel and led away through the suction channel so that one maintains a constant flow of fluid. At the same time the same quantity of fluid is led away through the suction channel as is supplied through the supply channel in order to maintain the excess pressure in the body cavity. According to the invention the suction channel has a larger cross section than the supply channel. This design permits detached tissue parts, so-called chips to be led away through the suction channel without previously having to remove the working insert from the outer shank. The arrangement thus permits chips to be continuously led away during an operation without the operation having to be interrupted for removal of the working insert from the resectoscope. In this manner an operation may be carried out in a manner which is less time-consuming and which is less of a burden to the patient. Since a continuous change of instruments is avoided, the required fluid balancing for avoiding the feared fluid-overload may be carried out more simply, securely and accurately. The suction channel in a first half of the cross section of the outer shank extends parallel to this. At the same time the suction channel preferably has a cross-sectional shape which corresponds essentially to half the cross section of the outer shank. In this manner one may create a very large suction channel which permits the suctioning away of larger chips. In a second half of the cross section of the outer shank, in its inside there extends an optics channel as well as at least one electrode guide tube outside the suction channel and parallel to the outer shank. This arrangement permits half of the inner cross section of the outer shank to be used for the suction channel, whilst the other half is used for the remaining channels, i.e. the optics channel as well as the at least one electrode guide tube. In this manner in the inside of the outer shank there is made available a very large suction channel.

Preferably at the distal end of the resectoscope, i.e. at the end proximal to the patient there is provided a cutter loop which delimits a cross sectional area which in its dimension is smaller or equal to the cross sectional area of the suction channel. The cutter loop serves for detaching tissue parts, as with known resectoscopes. For this the cutter loop is preferably designed as a U-shaped bow which is led through the tissue. The cross sectional area delimited by the cutter loop is determined by the loop size. The size of a detached tissue part or chip is defined by selection of the loop size. Since the loop size is selected such that the cross sectional area delimited by the cutter loop is smaller or equal to the cross sectional area of the suction channel, one may ensure that the detached chips have a size which is smaller than the cross section of the suction channel so that the chips may be safely led away through the suction channel. One may thus prevent the detached chips from sticking in the suction channel and blocking this.

The outer shank preferably has a circular cross section and the suction channel a semicircular cross section. In this manner the suction channel may fill half the inner space or the inner cross section of the outer shank and use it for transport of the chips. However other cross sectional shapes are also conceivable. Thus the outer shank for example may be formed ovally, wherein the suction channel has a cross sectional shape which corresponds essentially to half the inner cross section of the outer shank. The outer contour of the suction channel may be formed corresponding to the shape of the inner cross section of the outer shank, so that the space available in the inside of the outer shank may be optimally exploited.

The supply channel is preferably formed by the cross sectional space surrounding the suction channel, the optics channel as well as the electrode supply tube. This means the supply channel is not formed as a separate shank or as a separate tube as the discharge channel but is formed by the remaining free space in the inside of the outer shank. In this manner the cross section of the outer shank may be optimally exploited and no unused free spaces remain in the inside of the outer shank. Thus a sufficiently large cross section for the supply channel may be made available also with a large cross section of the outer shank according to the invention. The supply channel may have a cleaved cross sectional shape since only a fluid without large particles is to flow through it. The discharge channel on the other hand must have a large, non-fissured, coherent cross sectional area in order to allow the passage of chips.

Preferably there are provided two electrode guide tubes which are arranged on two diametrically opposed sides of the optics channel. The electrode guide tubes preferably have a smaller cross section or diameter than the optics channel. In this manner with a round or oval cross section of the outer shank one may optimally use the free space remaining for the optics channel as well as the electrode guide tubes, i.e. half the cross sectional area of the outer shank. If the suction channel fills half the inner cross section of the outer shank then with a round or oval cross section there remains a semicircular cross section or a cross section in the shape of a half oval. The optics shank with a larger diameter is preferably arranged centrally in order to optimally exploit the section of the greatest height of the cross sectional area. There is sufficient space for the electrode guide tubes in the remaining lateral regions with a smaller cross section. With this arrangement the two electrode guide tubes are furthermore arranged distanced as far as possible to one another. This permits a secure and in particular rotationally secure guiding of the cutter loop and thus a more precise separation of tissue parts. Alternatively the electrode may also be axially guided by way of an individual guide tube encompassing the optics.

With the first embodiment form the limbs of the cutter loop usefully extend parallel to the outer shank through the electrode guide tube. The cutter loop is formed bow-shaped or U-shaped. The two limbs are essentially bent at right angles so that the bow of the cutter loop extends bent at an angle in a plane and in particular transversely or normal to the further direction of extension of the limbs. Since the two limbs run parallel to the outer shank through the electrode guide tubes, the bow of the cutter loop thus extends bent at an angle in one plane and preferably essentially normally to the longitudinal axis of the outer shank. By way of linear movement of the limbs in the inside of the electrode guide tubes in their longitudinal direction the cutter loop is moved distally and proximally in order to detach tissue parts.

According to a preferred embodiment form the suction channel is further connected to a vacuum source via a first valve. In this manner by opening this valve one may produce a vacuum in the inside of the suction channel in order to suction off detached tissue parts or chips through the suction channel. The valve may be opened for a short time during operation so that detached chips may be suctioned away without having to interrupt the operation procedure.

Preferably the first valve is coupled to an actuation means for a cutter loop in a manner such that the valve is opened in a predefined position of the cutter loop. This position is preferably the proximal end position of the cutter loop in which the cutter loop is located after the procedure of separation of the tissue. By way of such a coupling of the valve to the actuation means for the cutter loop it is achieved that after completion of the separation procedure, the detached tissue part is directly suctioned away in that the valve is opened and a vacuum impulse is produced in the suction channel. The suctioning away of the detached tissue parts may thus be effected automatically at the correct point in time. Alternatively the valve may however also be actuated by the operator independently of the cutting procedure for example via a button or foot switch.

It is further preferred for the first valve to be activated via a time impulse means which opens the valve for a predefined time duration given an actuation signal, in order to produce a suction impulse in the suction channel. A suction impulse may be produced for a predefined time duration by way of this arrangement. This is important when suctioning in order to ensure that the excess pressure in the body cavity is not reduced to an extent such that this disintegrates or collapses. In this manner one may prevent too long an opening of the valve and a thus associated suctioning of too large a quantity of fluid. The suction impulses may be selected very short since it is not necessary to suction a detached chip directly through the complete suction channel out of the resectoscope. On the contrary it is indeed sufficient for the chip firstly only to be suctioned into the suction channel and for it to remain there. After separating the next chip when a new suction impulse is produced, the previously detached chip then travels further in the suction channel in the proximal direction when the subsequently detached chip is suctioned into the suction channel. This means that the detached chips travel in steps through the suction channel successively distanced to one another like the carriages of a train.

Usefully the first valve is arranged directly on or directly in a connection piece of the suction channel, i.e. essentially directly at the proximal end of the suction channel. This arrangement has the advantage that one does not need to arrange flexible tubings between the first valve and the connection piece at the proximal end of the suction channel. The arrangement of flexible tubings between the first valve and the suction channel with an impulsed suctioning has the disadvantage that on opening the first valve a vacuum prevailing at this leads to an elastic deformation, i.e. to a narrowing of the cross section of the flexible tubing between the valve and the suction channel. By way of this, on the one hand the suction power prevailing at the suction channel is reduced. On the other hand the flexible tubing with the subsequent closure of the valve on account of the sluggishness of the flow may elastically widen and thereafter may again relax in a spring-elastic manner, by which means the flow direction on account of the closed valve is deflected in the direction of the resectoscope, by which means cut-away tissue parts, in particular the last tissue part cut away, is rinsed out of the distally open suction channel back into the body cavity. This disadvantage is avoided by the arrangement of the first valve directly on the proximal end at the suction channel.

It is further preferred for a return valve to be provided on or in the proximal end of the suction channel which permits a flow only in the proximal direction. This return valve prevents a reversal of the flow direction by way of which detached tissue parts could be rinsed through the distal end of the suction channel back into the body cavity.

Preferably the valve is designed as a magnet valve which is activated by an electrical actuation signal. The electrical activation of the valve permits a very variable and simple adjustment of the opening duration of the valve. The magnet valve is preferably designed as a flexible tubing squeezer which clamps a suction flexible tubing. The clamping is released on opening the magnet valve so that fluid may flow through the suction flexible tubing in the direction of the vacuum source in order to be able to suction fluid and detached chips out of the body cavity.

According to a further preferred embodiment form the suction channel is connected to a discharge conduit for a continuous discharge of fluid via a second valve. If this second valve is opened a small quantity of rinsing fluid may be led away continuously through the discharge conduit, for example into a second collection container.

Preferably the second valve is coupled to the first valve in a manner such that the second valve is closed when the first valve is opened. This allows a small quantity of rinsing fluid to be continuously led out of a body cavity via the opened second valve and the discharge conduit even when the first valve is closed. The coupling of the first and the second valve may be effected in a purely control-technological manner if both valves are designed as magnet valves. In this case a control apparatus may activate the two valves such that either the second valve is opened in order to provide a continuous fluid discharge or the first valve is opened in order to lead away detached tissue parts out of the body cavity. By way of this measure it is achieved that detached chips may only get into the collection vessel envisaged for accommodating the tissue parts. Instead of coupling the two valves to one another by way of a suitable electrical activation in the described manner, a purely mechanical coupling is possible; thus both valves may be grouped together in a two-way valve which reciprocally releases a vacuum conduit or the discharge conduit. Such a two-way valve is preferably likewise designed as an electrically activated magnet valve.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1:
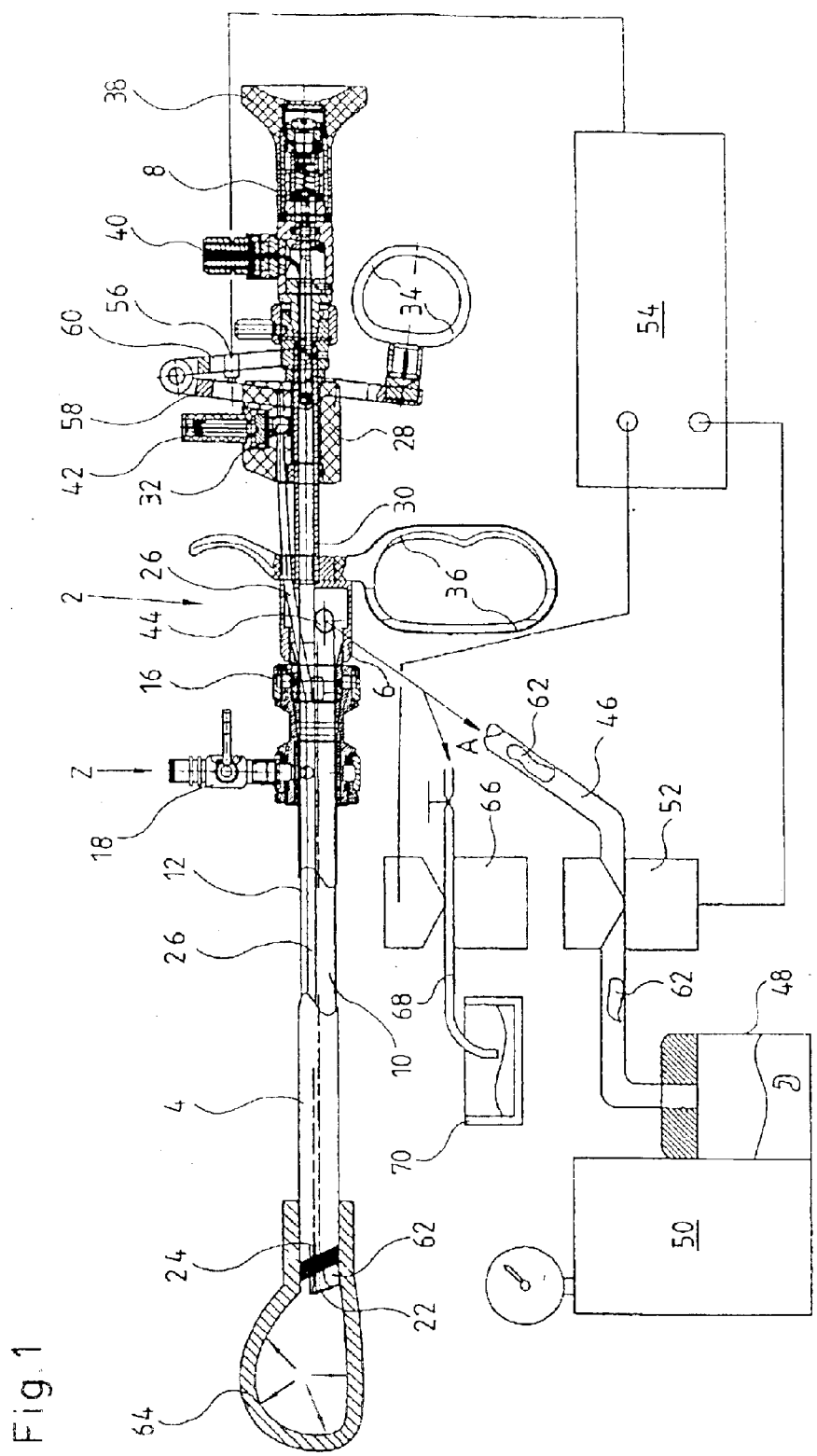
FIG. 1 a schematic sectional view of the resectoscope according to the invention.

FIG. 1 shows a schematic entire view of the resectoscope according to the invention with the associated peripheral apparatus. The actual resectoscope 2 consists essentially of three parts, specifically a tubular outer shank 4, the working insert 6 as well as the optics 8. The working insert 6 is inserted into the shank from the proximal end of the shank 4. The working insert 6 comprises a suction channel 10 formed by a tube which is separate from the outer shank, an optics shank 12 as well as two electrode guide tubes 14 as is shown in the front end view of FIG. 2. The suction channel 10, the optics shank 12 as well as the electrode guide tubes 14 extend parallel to the longitudinal axis of the shank 4 through this up to the distal end of the shank 4. The working insert 6 is connected to the proximal end of the shank 4 via a known coupling cone connection 16. The shank 4 in the vicinity of its proximal end further comprises a blockable instrument cock 18 on which a supply conduit for a rinsing fluid is connected. The supply is indicated in FIG. 1 by the arrow Z. The instrument cock 18 is connected to the inside of the shank 4 which, as will be explained in more detail further, forms a supply channel 20.

A cutter loop 22 exiting out of the distal end of the shank 4 is formed bow-shaped with angularly bent limbs 24 which extend through the electrode guide tubes 14 proximally in the longitudinal direction of the shank 4. In the working insert 6 in the connection to the proximal end of the shank 4 there is formed a channel 26 through which the cutter loop or the limbs 24 of the cutter loop extend. Furthermore on the working insert 6 there is provided a lock body 28 displaceable in the longitudinal direction of the shank 4. The lock body 28 is displaceable in the proximal-distal direction on a proximally extending shank 30. The proximal end of the cutter loop 22 or the proximal ends of their limbs 24 is fixed via a preferably spring-biased tension lock 32 in the lock body 28. The lock body 28 is coupled to a movable handle part 34. Additionally a fixed handle part 36 is provided on the working insert. By moving the movable handle part 34 toward the fixed handle part 36 the lock body 28 coupled to the movable handle part 34 is moved in the distal direction, i.e. towards the patient. At the same time the cutter loop 22 moves distally away from the distal end of the shank 4. If the movable handle part 34 is moved away from the fixed handle part 36, the lock body 28 is displaced or retracted on the shank 30 in the proximal direction, i.e. it moves away from the patient. With this movement the cutter loop 22 via its limbs 24 is likewise retracted in the proximal direction. I.e. the cutter loop 22 approaches the distal end of the shank 4 and is pulled into the shank 4. At the same time the cutter loop 22 may separate a tissue part if it is pulled through a tissue section.

The optics 8 designed in the known manner is inserted into the shank 30 from the proximal end of the working insert 6. The optics 8 comprise an eyepiece 38 as well as a fibre-optic connection 40.

An HF-connection is provided on the lock body 28 or on the tension lock 32. A supply of current to the limbs 24 and the cutter loop 22 for coagulation is effected via this HF-connection 42. In the known manner a so-called neutral electrode (not shown here) is applied onto the body surface of the patient as a second pole. In order to avoid an unintended current transmission to the operator and/or patient, the lock body 28 is preferably manufactured of a non-conducting material, for example plastic, and the limbs 24 between the U-shaped cutter loop bent at angles at the distal end and the proximal connection end, i.e. the end which is fixed in the tension lock 32, are provided with an insulating coating. With this it may be the case of a shrink flexible tubing or likewise.

The suction channel 10 is connected to a flexible tubing connection piece 44 in the working insert 6. The discharge or suctioning of the rinsing fluid is effected through this flexible tubing connection piece, as is indicated by arrow A in FIG. 1. The flexible tubing connection piece 44 is connected to a vacuum conduit 46. The suction or vacuum conduit 46 is connected to a collection vessel 48 which for its part is in connection with a vacuum source 50. The vacuum source 50 produces a vacuum in the collection vessel 48 of preferably about 60 to 90 kPa, even more preferred about 85 kPa.

A magnet valve 52 is provided in the suction flexible tubing 46. In the shown case the magnet valve 52 is designed as a clamping valve which clamps the suction flexible tubing 46 from the outside. Such a valve is preferred for reasons of cleaning, but one may also apply other magnet valves for blocking the suction conduit 46. A control apparatus 54 transmits an opening signal to the magnet valve 52 in order to open the magnet valve 52. At the same time the opening duration of the magnet valve is set or predefined via the control apparatus 54.

The control apparatus 54 for its part is activated via a button arranged in the mechanics of the movable handle part 34. The movable handle part 34 comprises two limbs 58 and 60 linkedly connected to one another. The limb 58 is connected to the handle part 34 as well as movably or rotatably connected to the lock body 28. The limb 60 is pivotably connected to the working insert 6 or to the shank 30. The contact or button 56 is arranged between the two limbs 58 and 60 so that it is actuated if the limb 58 is moved towards the limb 60 in order to retract the lock body 28 and thus the cutter loop 22 in the proximal direction and to detach a tissue part. At the same time the button 56 is preferably arranged such that it is actuated when the cutter loop 22 is in its proximal end position, i.e. a separating procedure of a tissue part has been completed. In this moment the button 56 produces an actuation impulse which is led further to the control means 54. Thereupon this opens the magnet valve 52 for a certain time duration. The time duration for a suction impulse predefined by the control apparatus is selected such that the suction impulse is sufficiently long in order to suction a tissue strip 62 detached by the cutter loop 22 into the suction channel 10. The suction impulse should not be so long that too large a quantity of fluid is suctioned out of the body cavity 64, which could cause the body cavity to collapse. For example a very short suction impulse of 0.1 sec duration may be sufficient. The previously detached and suctioned tissue strip 62 in steps with each subsequent separation of a tissue strip 62 with an associated suction impulse travels further through the suction channel 10 and the suction flexible tubing 64 up to into the collection vessel 48.

Figure 2:
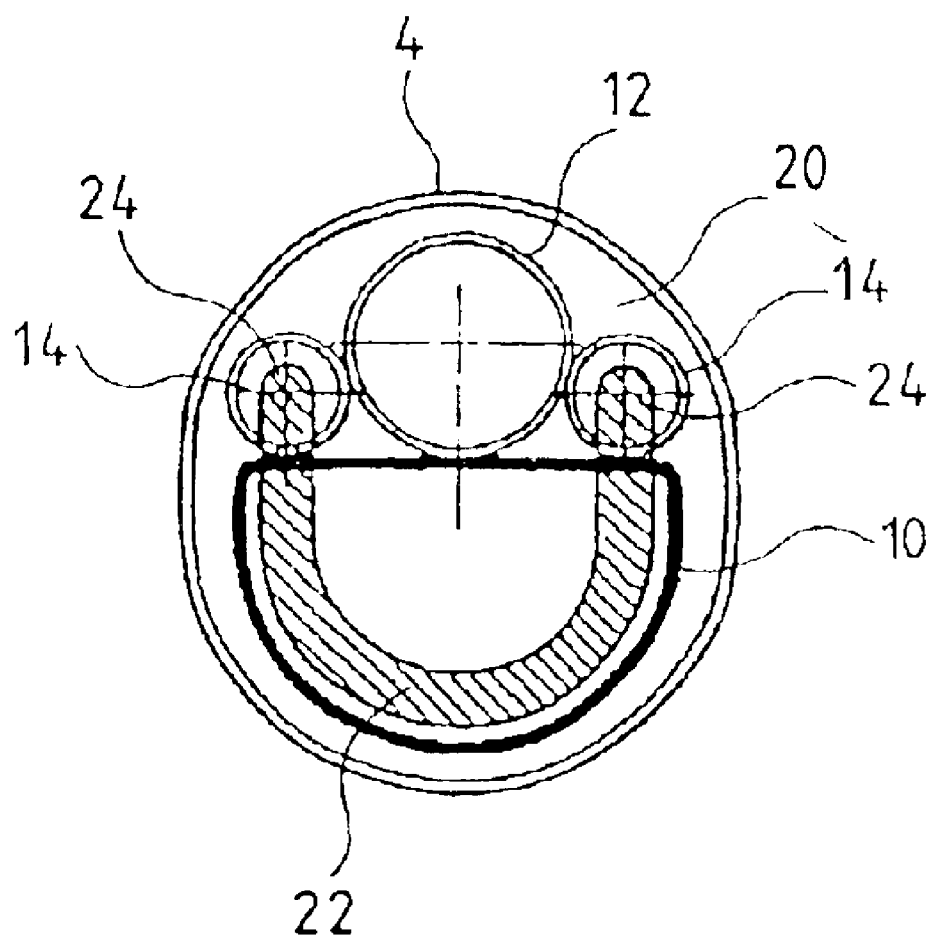
FIG. 2 a plan view of the distal end of the resectoscope shank.

FIG. 2 shows a plan view of the distal end of the shank 4. The shank 4 which forms an outer shank has an essentially oval cross sectional shape. The discharge or suction channel 10 is arranged in a first, in FIG. 2 lower half of the inner cross section. The suction channel 10 has an essentially semicircular cross sectional shape or a cross sectional shape of half an oval corresponding to the inner cross section of the shank 4. It thus essentially fills half the inner cross section of the shank. This arrangement permits a design of a very large suction channel 10, which permits detached tissue sections or tissue strips to be suctioned away during an operation without removing the working insert from the shank 4. The optics shank as well as the two electrode guide tubes 14 is arranged in the second, in FIG. 2 upper half of the inner cross section of the shank 4. All shanks or channels extend parallel to one another. The optics shank 12 is arranged centrally whilst the two electrode guide tubes 14 are arranged distanced to one another laterally of the optics channel 12. This arrangement permits optimal exploitation of the cross sectional space of the shank 4. Furthermore the distanced arrangement of two electrode guide tubes 14 permits an improved and more precise guiding of the cutter loop 22. The free space 20 surrounding the electrode guide tubes 24, the optics shank 12 as well as the suction channel 10 in the inside of the shank forms the supply channel. In this manner the inner cross section of the shank 4 is fully exploited. A rinsing fluid may be led through the supply channel into the inside of a body cavity in order to produce an excess pressure in this.

Simultaneously a predefined quantity of rinsing fluid may be discharged through the discharge channel in order to ensure a continuous rinsing. For this in a preferred embodiment form there is provided a second valve 66 which may release a discharge conduit 68 which likewise is in connection with the suction channel 10. If the second valve is opened a continuous fluid discharge, preferably alone due to gravity, takes place through the flexible tubing conduit 68 to a collection container 70. For suctioning away detached tissue parts the valve 52 is opened for a predefined time duration so that the tissue parts or chips may be suctioned into the collection container 48. The valve 66 is closed simultaneously or shortly before in order to interrupt the continuous discharge of the rinsing fluid for a defined time duration of the suction impulse. In this manner the chips may be collected in a separate collection container 48.

The cutter loop is formed U-shaped or bow-shaped. The shape of the bow at the same time preferably corresponds essentially to the outer contour of the suction channel 10 or the outer shank 4. The cross section enclosed by the bow of the cutter loop 22 is preferably smaller or equal to the cross section of the suction channel 10. In this manner it is achieved that the detached tissue pieces in any case are smaller than the cross section of the suction channel 10 so that a blocking or clogging of the suction channel 10 may be prevented when suctioning away the tissue pieces 62. If the bow shape of the cutter loop 22 is designed corresponding to the contour of the suction channel 10, additionally one may achieve a shearing effect between the distal edge of the outer shank 4 and the cutter loop 22 for a clean detachment of tissue pieces. The limbs of the bow-like cutter loop 22 are bent at an angle, preferably essentially at right angles. The limbs 24 extend through the electrode guide tubes 14 parallel to the longitudinal direction of the shank 4. On account of the angularly bent design the bow or the actual cutter loop 22 at the distal end of the resectoscope is angularly bent in a plane, in particular normal to the longitudinal axis of the shank 4. The arrangement of two distanced electrode guide tubes 14 permits a stable and extremely precise guiding of the cutter loops 22 since in particular a twisting is prevented on account of the distanced guides. However also a single guide tube encompassing the optics may selectively be provided for axially guiding the electrode.

For separating a tissue part the distal end or the resectocope 2 in a body cavity, for example a uterus, is brought to the desired position at which a tissue part is to be detached. With this one may observe the operating space through the applied optics. Subsequently the movable handle part 34 is retracted, i.e. is removed from the fixed handle part 36 in the proximal direction, wherein the cutter loop 22 via the limbs is retracted towards the distal end of the suction channel 10. At the same time the cutter loop 22 slides through the tissue and detaches a tissue strip 62b. If the movable handle part 34 and thus the cutter loop 22 have achieved a predefined end position a suction impulse is produced via the button 56 and the control means 54, which suctions the detached tissue part 62 into the suction channel 10. Subsequently the cutter loop 22 is again moved into its distal original position. This is effected by moving the movable handle part 34 again toward the fixed handle part 36. Advantageously a spring may be provided between the limbs 58 and 60 in order to automatically move the movable handle part 34 distally or proximally.

Figure 3:
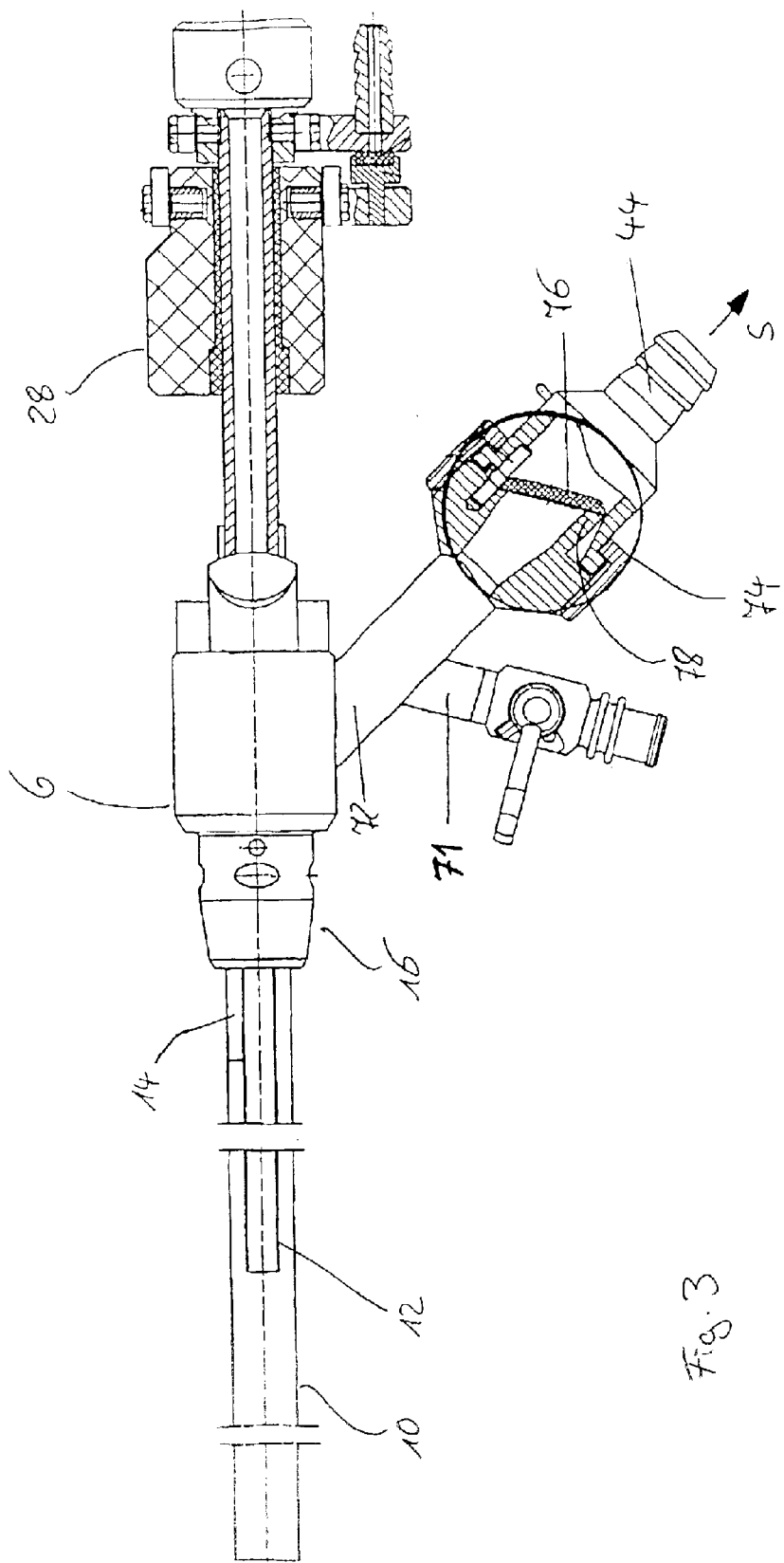
FIG. 3 a partly sectioned lateral view of the proximal end of the resectoscope according to a second embodiment form.

FIG. 3 shows a partly sectioned lateral view of a working insert 6 according to a second embodiment form of the invention. The working insert 6 corresponds essentially to the previous resectoscope or working insert 6 described previously by way of FIGS. 1 and 2. The suction channel 10, the optics shank 12 as well as the electrode guide tubes 14 extend distally from the working insert 6. The working insert 6 comprises a coupling cone connection 16 via which the working insert 6 is fixed on the shank 4. At the proximal end, as described above, there is arranged the lock body 28. From the working insert 6 there further extends an instrument cock 71 to which the flexible tubing conduit 68 (see FIG. 1) for a continuous discharge of rinsing fluid is connected. Apart from the instrument cock 71 a connection tube 72 is connected to the suction channel 10 at its proximal end. At the proximal end of the connection tube 72 there is formed the flexible tubing connection piece 44 for connection to a vacuum conduit 46 or a suction flexible tubing 46. The second embodiment form shown in FIG. 3 differs from the embodiment form according to FIGS. 1 and 2 in that a return valve 74 is arranged in the connection tube 72 in the flow direction S in front of the flexible tubing connection piece 44. The return valve 74 permits a flow only in the suction direction, i.e. from the distal end towards the proximal end of the suction channel. The shown return valve for this has a membrane 76 which in the closed condition bears on an annular shoulder 78. At the same time the annular shoulder 78 is provided at that side of the membrane which is to the rear in the flow direction so that with a flow reversal opposite to the flow direction S the membrane 76 is deflected against the annular shoulder 78. If a vacuum is applied on the flexible tubing connection piece 44, this effects a flow in the direction S wherein the membrane 76 is deflected in the flow direction S and releases the flow passage.

The arrangement of the return valve 74 has the advantage that a pressure increase in a vacuum conduit 46, as may for example arise with elastic flexible tubings and a pulsed suction operation on account of the springing back of the flexible tubing wall, may not lead to a rinsing back of particles through the suction channel 10 into the body cavity.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A resectoscope comprising:
   a tubular outer shank having a cross-section;
   a suction channel formed by a tube which is separate from the outer shank and extends parallel to the outer shank inside the cross-section, said suction channel having a cross-sectional area;
   an optics channel extending parallel to the shank inside the cross-section and outside of the suction channel;
   at least one electrode guide tube extending parallel to said shank inside the cross-section and outside of the suction channel; and
   a supply channel in said cross-section extending parallel to said outer shank outside of the suction channel and having a cross-sectional area which is smaller than the cross-sectional area of said suction channel.

2. A resectoscope as in claim 1 wherein said outer shank has a distal end and a proximal end, said resectoscope having a cutter loop which delimits a cross-sectional area which is less than or equal to the cross-sectional area of the suction channel.

3. A resectoscope as in claim 1 wherein said outer shank has one of a circular, and an oval cross-section, and said suction channel has one of a semi-circular and a semi-oval cross-section.

4. A resectoscope as in claim 1 wherein said supply channel occupies a remaining portion of said cross-sectional area which is not occupied by said suction channel, said optics channel, and said at least one electrode guide tube.

5. A resectoscope as in claim 2 comprising two of said electrode guide tubes arranged on opposed sides of said optics channel.

6. A resectoscope as in claim 5 wherein said cutter loop comprises a pair of parallel limbs which extend parallel to the shank through respective said electrode guide tubes.

7. A resectoscope as in claim 1 further comprising a vacuum source which is connected to said suction channel via a first valve.

8. A resectoscope as in claim 7 further comprising means for actuating said cutter loop, said means being coupled to said first valve so that said first valve is opened in a pre-defined position of said cutter loop.

9. A resectoscope as in claim 8 further comprising control apparatus which opens said first valve for a predetermined duration in response to an actuation signal from said means for actuating said cutter loop.

10. A resectoscope as in claim 7 further comprising a connection piece for said suction channel, said first valve being arranged in said connection piece.

11. A resectoscope as in claim 7 further comprising a return valve at the proximal end of the suction channel.

12. A resectoscope as in claim 7 wherein said first valve is a solenoid valve which is activated by an electrical actuation signal.

13. A resectoscope as in claim 7 further comprising a discharge conduit which is connected to said suction channel via a second valve for a fluid discharge.

14. A resectoscope as in claim 13 wherein the second valve is coupled to the first valve so that the second valve is closed when the first valve is opened.

* * * * *

UNITED STATES PATENT AND TRADEMARK OFFICE
CERTIFICATE OF CORRECTION

PATENT NO. : 6,824,544 B2 Page 1 of 1
APPLICATION NO. : 10/396173
DATED : November 30, 2004
INVENTOR(S) : Manfred Boebel It is certified that error appears in the above-identified patent and that said Letters Patent is hereby corrected as shown below:

Title page should read
[75] Inventors:  Manfred Boebel, Bauscholtt (DE);
                   Ludwig Bonnet, Knittlingen (DE);
                   Sybille Brüstle, Stermenfels (DE)

Signed and Sealed this

Twenty-ninth Day of August, 2006

JON W. DUDAS
*Director of the United States Patent and Trademark Office*